United States Patent [19]

Kulik et al.

[11] Patent Number: 4,643,712
[45] Date of Patent: Feb. 17, 1987

[54] AORTIC CANNULA

[75] Inventors: Yaroslav P. Kulik, Blagoveschensk; Ivan I. Shmyrin, Vladivostok; Rustam I. Utyamyshev; Marina N. Vyrzhikovskaya, both of Moscow, all of U.S.S.R.

[73] Assignee: Blagoveschensky Gosudarstvenny Meditsinsky Institut, Blagoveschensk, U.S.S.R.

[21] Appl. No.: 789,144

[22] Filed: Oct. 18, 1985

[51] Int. Cl.⁴ .................. A61M 1/03; A61M 25/00
[52] U.S. Cl. ........................... 604/4; 604/249; 604/256; 604/264
[58] Field of Search .................. 604/4, 43, 93, 256, 604/249, 264, 280–284

[56] References Cited

U.S. PATENT DOCUMENTS

| 1,566,061 | 12/1925 | Ziegler | 604/256 |
| 3,030,953 | 4/1962 | Koehr | 604/166 |
| 3,565,074 | 2/1971 | Foti | 604/170 X |
| 4,129,129 | 12/1978 | Amrive | 604/43 X |
| 4,248,224 | 2/1981 | Jones | 604/284 X |
| 4,301,797 | 11/1981 | Pollack | 604/256 |

OTHER PUBLICATIONS

Sarns, Cardiovascular Accessories; Aug. 1982.

Primary Examiner—Dalton L. Truluck
Attorney, Agent, or Firm—Fleit, Jacobson, Cohn & Price

[57] ABSTRACT

An aortic cannula, including a head which has a front end adapted for being inserted into the aorta, and a base communicating with a blood supply tube; the head is shaped as an oblate cone that flares out from the front end which is an ellipse in cross-section, towards the base which is a circle in cross-section, while the tube is provided with a plurality of through holes or perforations located in an immediate vicinity of the place where it is joined with the base, and has a slidable sleeve adapted to operatively cover the perforations.

2 Claims, 6 Drawing Figures

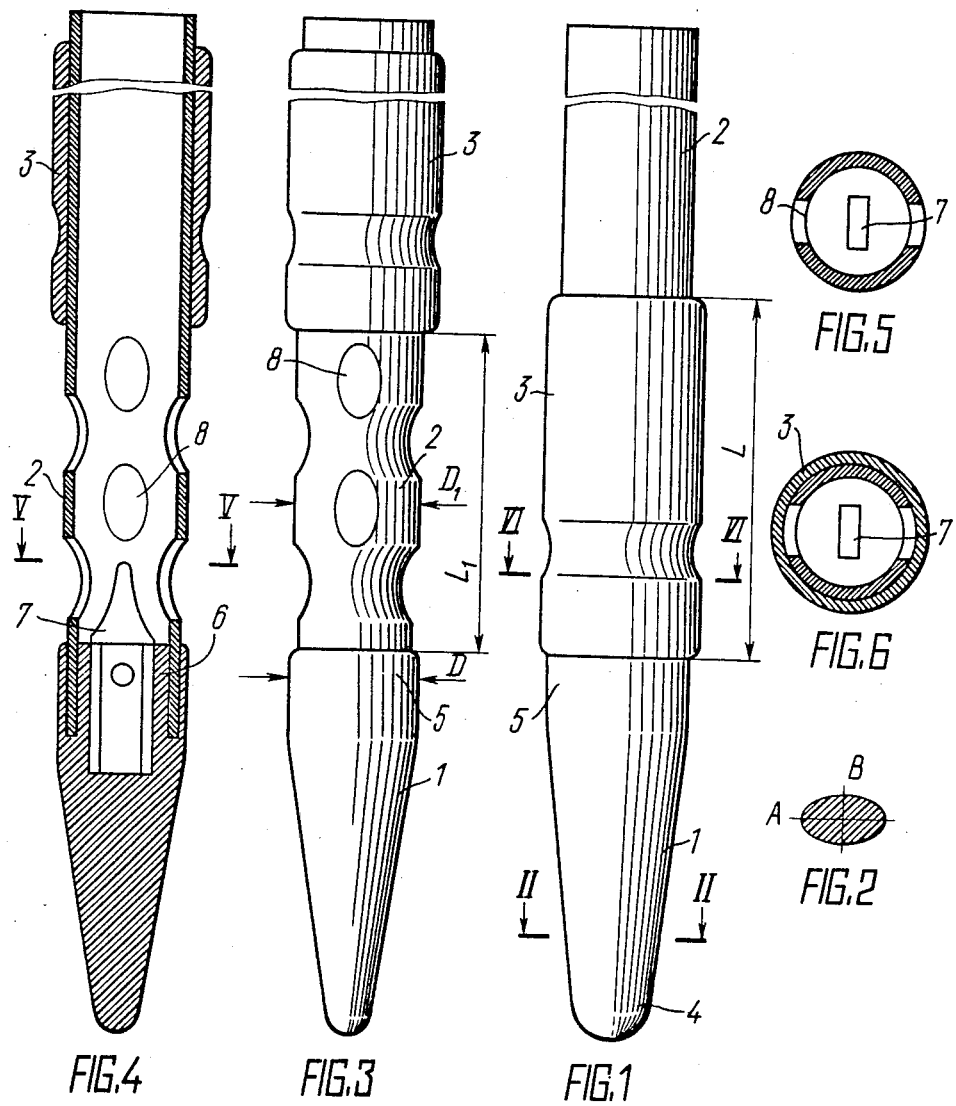

4,643,712

AORTIC CANNULA

FIELD OF THE INVENTION

The present invention relates generally to medical engineering, in particular, to surgical instruments made use of in thoracic surgery involved in extracorporeal circulation for blood return to patient's general circulation from an extracorporeal circulation ('heart-lung') apparatus through the aorta, and more specifically, to aortic cannulas. Every surgical prodecure on the heart or cardiac vessels carried out under extracorporeal circulation conditions, involves cannulation of the ascending aorta in order to return the blood from the 'heart-lung' apparatus to patient's circulation system. Principal requirements that determine the quality of performance of the aforesaid stage or surgery and should be met by the cannula construction, are as follows: prevention of any injury to the aortic tissues and of blood loss (hemorrhage) accompanying cannula insertion and happening to be lethal in some particular cases; reduction of the blood flow turbulence and hence of the hemolysis process in case of prolonged perfusion procedures; prevention of the onset of aeroembolism resulting from insertion of a cannula into the aorta, and so on.

BACKGROUND OF THE INVENTION

There are known prior-art cannulas for blood return to patient's circulation system through the aorta (cf. a catalogue of Aortic Arch Cannula by Sarns Co), consisting of transparent tubes rigidly connected to a head which is in fact a straight or curved radially form, and is essentially another tube but having a smaller bore diameter than the blood supply tube. A stop restricting the depth of the cannula insertion into the aortic incision, is provided at the place where the blood supply tube is joined with the head. The head front end has a bevel edge to facilitate insertion of the cannula into the aortal incision. However, the construction of the cannula involved, whose head is tubular in shape fails to rule out traumatic lesion inflicted upon the aortic tissues during insertion of the cannula into the aortic incision and causes additional loss of blood. In addition, the aforedescribed annula construction makes it impossible to hermetically seal the cannula in order to evacuate air from its interior before being inserted into patient's aorta, which might result in air bubbles penetrating into the aorta.

The disadvantages mentioned above are partly obviated in a venous catheter (cf. a catalogue of Venous Catheter by Sarns Co) used for blood sucking out of the venae cavae and the cardiac atrium of a patient. The venous catheter comprises an elastic transparent tube rigidly coupled to a cone-shaped head which facilitates its insertion into the vessel. Through holes are provided on the head lateral surfaces for passing the blood sucked out of the patient's venae cavae and the cardiac atrium during extracorporeal circulation.

The venous catheter of the construction described above cannot be applied for blood return to patient's aorta, since the head having only lateral holes causes turbulence of the blood flow supplied by the 'heart-lung' apparatus. Besides, the construction of such a catheter having the head with through lateral holes, is not air-tight so that there is a risk of air bubbles penetrating into patient's aorta.

DISCLOSURE OF THE INVENTION

It is an object of the present invention to provide an aortic cannula for blood return into patient's circulation system through the aorta in extracorporeal circulation whose construction, due to the shape of the head, rules out completely the danger of inflicting injury to the aortic tissues and penetrating air bubbles into the aorta.

Said and other objects are accomplished due to the fact that in an aortic cannula, comprising a head which has a front end adapted for being inserted into the aorta, and a base communicating with a blood supply tube, according to the invention, the head is shaped as an oblate cone that flares out from the front end towards the base, the front head end being an ellipse in cross-section, while the head base is essentially a circle carrying a blood flow divider, the flow of blood passing along a tube provided with slidable sleeve and having at least two through holes made in its walls immediately at the head base.

The cannula construction features described above rule out completely the danger of inflicting traumatic lesion upon the aortic tissues and the loss of blood resulting from insertion of the head of the cannula into the aorta, reduce the turbulence of the blood flow supplied, as well as fully precludes the risk of air bubbles penetrating into patient's blood (aeroembolism).

It is expedient that the greater axis of the ellipse of the front head end be much longer than the lesser axis thereof, and that the ratio between the lengths of the ellipse axes should decrease gradually in a direction from the front head end towards its base, the diameter of said base being equal to the tube outside diameter.

Such a shape of the head enables it to be inserted into the aortic incision without injuring the surrounding tissues and thus enlarging gradually the aortic incision, thereby precluding loss of blood.

It is likewise expedient that the blood flow divider be pointed against the flow of blood.

It is by no means less expedient that the through holes in the tube walls be arranged staggerwise in the mutually square planes and that part of said holes be situated opposite to the blood flow divider.

Such a mutual arrangement of the blood flow divider and the through holes in the tube walls reduces the blood flow velocity and its turbulence, which decreases hemolysis during prolonged perfusion procedures.

It is preferable that the length of the slidable sleeve should exceed the length of the tube perforated portion.

This makes it possible to hermetically seal the perforations in the tube walls and to fill its interior with physiological saline or blood to expell air therefrom before its being inserted into the aorta.

BRIEF DESCRIPTION OF THE DRAWINGS

Given below is a detailed description of a specific illustrative embodiment of the present invention with reference to the accompanying drawings, wherein:

FIG. 1 is a general schematic view of an aortic cannula showing the slidable sleeve in a position where it covers the perforated tube portion, according to the invention;

FIG. 2 is a section taken along the line II—II in FIG. 1, according to the invention;

FIG. 3 is a general schematic view of an aortic cannula showing the slidable sleeve in a position where it covers, according to the invention;

FIG. 4 is a longitudinal section view of an aortic cannula, according to the invention;

FIG. 5 is a section taken along the line V—V in FIG. 4, according to the invention; and FIG. 6 is a section taken along the line VI—VI in FIG. 1, according to the invention.

BEST MODE OF CARRYING OUT THE INVENTION

The aortic cannula as disclosed in the present invention consists of a head 1 (FIG. 1) rigidly coupled to a blood supply tube 2 which communicates with the mainline of an extracorporeal circulation ('heart-lung') apparatus (omitted in the Drawing), and a slidable sleeve 3 arranged on the blood supply tube 2 coaxially therewith.

The head of the aortic cannula is shaped as an oblate cone and comprises a front end 4 and a base 5, the cone of the head flaring out from the front end towards the base 5.

The front end 4 of the head 1 is essentially an ellipse in cross-section (FIG. 2), wherein the greater axis "A" is much longer (at least 1.5 to 2 times) than the lesser axis "B" thereof, i.e., A>B. The ratio between the lengths of the greater axis A and the lesser axis B of the ellipse decreases in a direction from the front end 4 of the head 1 towards the base 5 thereof in such a manner that the length of the greater axis A becomes equal to the length of the lesser axis B at the base 5 of the head 1, i.e., A=B. Thus, the base 5 (FIG. 3) of the head 1 is in fact a circle in cross-section, the diameter D of said circle being equal to the diameter $D_1$ of the blood supply tube 2, i.e., $D=D_1$.

A blood flow divider 7 is provided at the end face 6 (FIG. 4) of the base 5 of the head 1 inside the blood supply tube 2, the pointed end of said blood flow divider facing against the flow of the blood. The blood supply tube 2 is rigidly coupled to the base 5 of the head 1.

A plurality of through holes or perforations 8 are made in the walls of the blood supply tube 2, said holes running from the end face 6 of the base 5 of the head 1 and arranged staggerwise on the blood supply tube 2 (FIG. 4). Some of the holes 8 put at least two of these, are situated opposite to the blood flow divider 7 (FIG. 5). A slidable sleeve 3 (FIGS. 3, 6) is fitted on the blood supply tube 2 coaxially with its axis of symmetry. The length L of the sleeve 3 (FIG. 1) exceeds the length $L_1$ of the portion of the blood supply tube 2 provided with the holes 8 (FIG. 3), i.d., $L>L_1$.

The aortic cannula of the invention functions as follows.

Prior to inserting the aortic cannula into the aortic incision (omitted in the FIGURE), the holes 8 in the blood supply tube 2 are closed with the slidable sleeve 3 by moving the latter along the tube 2 till it meets the base 5 of the head 1. Then the tube 2 of the cannula is filled physiological saline or blood to expell air therefrom. Next the front end 4 of the head 1 is inserted into the aortic incision, gradually enlarging the latter. The head 1 is introduced into the aorta till the front end of the slidable sleeve rests against the aortic wall. During a further progress of the cannula inside the aorta the sleeve 3 remains immovable and forced against the aortic wall, while the blood supply tube 2 travels inside the sleeve 3 lengthwise its axis. As a result, the holes 8 in the tube 2 that have already got inside the aorta, are exposed one after another.

Once the portion of the tube 2 provided with the holes 8 has been inserted into the aorta, the blood supplied from the 'heart-lung' apparatus begins to be fed to the patient's circulation.

Thus, the aortic cannula made according to the present invention, though being comparatively simple in construction, enables one to preclude injury to the aortic tissues and rule out completely the loss of blood accompanying the insertion of the cannula into the aortic incision, as well as to considerably reduce the turbulence of the blood flow and hence hemolysis, especially during prolonged perfusion procedures. In addition, the aortic cannula of the invention makes it possible to completely rule out the danger of aeroembolism during blood return through the aorta in case of extracorporeal circulation. All the advantages enlisted hereinabove contribute to a favourable outcome of the surgery performed.

What is claimed is:

1. An aortic cannula for return of blood to a patient during extracorporeal circulation, said cannula comprising:
   a head shaped as an oblate cone and including a front end adapted to be inserted into an aorta and being elliptical in cross-section and further including a base being circular in cross-section, said head flaring outwardly in a direction from said front end towards said base, a ratio between the lengths of a greater axis and a lesser axis of said elliptical front end decreases in a direction from said front end towards said base;
   a blood flow divider mounted on said base and having a pointed shape, a pointed end of said divider facing opposite to the direction of blood flow in said cannula;
   a tube communicating with said base and adapted for blood supply to said base, said tube having perforations staggered along a portion immediately adjacent to said base and including some perforations located opposite to said blood flow divider; and
   a sleeve slidably fitted on said tube, the length of said sleeve being greater than said portion of said tube which includes said perforations so that said sleeve moved between a first position covering said perforations and a second position uncovering said perforations.

2. An aortic cannula for returning blood to a patient's blood circulation system during extracorporeal circulation, said cannula comprising:
   a head shaped as an oblate cone and having a front end adapted to be inserted into the aorta and having a cross-section in the shape of an ellipse, the size of a major axis of said front end exceeds the size of a minor axis of said front end, a ratio of the size of the major axis to the minor axis of said front end decreasing in a direction away from said front end and further having a base having a cross-section in a circular shape so said head flares outwardly in a direction away from said front end toward said base;
   a blood flow divider provided on said base and having a pointed shape, the pointed end of said divider facing in a direction opposite to the direction of blood flow;
   a tube communicating with said base for supplying blood to said base, said tube having in a portion located immediately adjoining said base, at least two through holes opposite said blood flow divider; and
   a sleeve having a length greater than a length of said portion of said tube, and said sleeve being mounted on said tube so that said tube slides within said sleeve to cover and uncover said through holes, which is provided with said holes.

* * * * *